(12) United States Patent
Zhao et al.

(10) Patent No.: US 12,694,534 B2
(45) Date of Patent: Jul. 28, 2026

(54) DETECTION METHOD FOR INFRARED THERMAL IMAGE DAMAGE AREA OF COAL ROCK

(71) Applicant: China University of Mining and Technology, Xuzhou (CN)

(72) Inventors: Xiaohu Zhao, Xuzhou (CN); He Tian, Xuzhou (CN); Peng You, Xuzhou (CN); Tingyu Che, Xuzhou (CN)

(73) Assignee: China University of Mining and Technology, Xuzhou (CN)

( * ) Notice: Subject to any disclaimer, the term of this patent is extended or adjusted under 35 U.S.C. 154(b) by 194 days.

(21) Appl. No.: 18/806,740

(22) Filed: Aug. 16, 2024

(65) Prior Publication Data

US 2025/0061701 A1     Feb. 20, 2025

(30) Foreign Application Priority Data

Aug. 17, 2023     (CN) .......................... 202311037199.0

(51) Int. Cl.
G06T 7/11          (2017.01)
G06N 3/0455        (2023.01)
(Continued)

(52) U.S. Cl.
CPC .............. G06T 7/11 (2017.01); G06N 3/0455 (2023.01); G06N 3/0464 (2023.01); G06T 5/60 (2024.01);
(Continued)

(58) Field of Classification Search
CPC ......... G06T 7/10–12; G06T 7/136–174; G06T 7/187; G06T 7/194; G06T 2207/10048;
(Continued)

(56) References Cited

FOREIGN PATENT DOCUMENTS

CN          113177965 A  *  7/2021   ............. G06N 3/045

OTHER PUBLICATIONS

Xiaohu, Z. H. A. O., et al. "Segmentation method of the abnormal area of coal infrared thermal image." Journal of Mine Automation 48.9 (2022): 92-99. (Year: 2022).*
(Continued)

*Primary Examiner* — Geoffrey E Summers
(74) *Attorney, Agent, or Firm* — Bayramoglu Law Offices LLC

(57)          ABSTRACT

A detection method for infrared thermal image damage area of coal rock includes: step 1: collecting and recording the infrared thermal image of coal rock in the process of loading destruction; step 2: processing a gray-scale transformation on the collected infrared thermal image of coal rock; step 3: denoising an infrared thermal image of coal rock after the gray-scale transformation by the dense residual image denoising algorithm of autocorrelation network; step 4: conducting an area segmentation on the infrared thermal image of coal rock after denoising to extract eigenvalues by using a coal-rock infrared thermal image damage area segmentation algorithm of improved encoder-decoder network; step 5: observing the damage area of coal rock. The detection method improves the denoising effect of the infrared thermal image of coal rock, strengthens the extraction of the characteristics of the damage area, and improves the accuracy of the segmentation.

4 Claims, 10 Drawing Sheets

(51) Int. Cl.

| | |
|---|---|
| *G06N 3/0464* | (2023.01) |
| *G06T 5/60* | (2024.01) |
| *G06T 5/70* | (2024.01) |
| *G06V 10/30* | (2022.01) |
| *G06V 10/80* | (2022.01) |
| *G06V 10/82* | (2022.01) |
| *G01N 25/72* | (2006.01) |
| *G01N 33/24* | (2006.01) |

(52) U.S. Cl.
CPC ............... *G06T 5/70* (2024.01); *G06V 10/30* (2022.01); *G06V 10/806* (2022.01); *G06V 10/82* (2022.01); *G01N 25/72* (2013.01); *G01N 33/24* (2013.01); *G06T 2207/10048* (2013.01); *G06T 2207/20084* (2013.01)

(58) Field of Classification Search
CPC ... G06T 2207/20084; G06T 5/60; G06T 5/00; G06T 2207/20081; G06T 5/70; G06V 10/26; G06V 10/30; G06V 10/806; G06V 10/7715; G06N 3/0455; G06N 3/0464; G06N 3/045; G06N 3/04; G01N 25/72; G01N 33/24

See application file for complete search history.

(56) References Cited

OTHER PUBLICATIONS

Hu, Xiaowan, et al. "Pseudo 3D Auto-Correlation Network for Real Image Denoising." 2021 IEEE/CVF Conference on Computer Vision and Pattern Recognition (CVPR). IEEE, 2021. (Year: 2021).*

Gao, Qiangqiang, et al. "Research on the denoising method of infrared thermogram during rock fracture." Infrared Physics & Technology 131 (2023): 104651. (Year: 2023).*

Gou, Yuanbiao, et al. "Multi-scale adaptive network for single image denoising." Advances in Neural Information Processing Systems 35 (2022): 14099-14112. (Year: 2022).*

Mehta, Sachin, et al. "ESPNet: Efficient Spatial Pyramid of Dilated Convolutions for Semantic Segmentation." European Conference on Computer Vision. Cham: Springer International Publishing, 2018. (Year: 2018).*

Xiong, Yu-Jie, et al. "Attention u-net with feature fusion module for robust defect detection." Journal of Circuits, Systems and Computers 30.15 (2021): 2150272. (Year: 2021).*

* cited by examiner

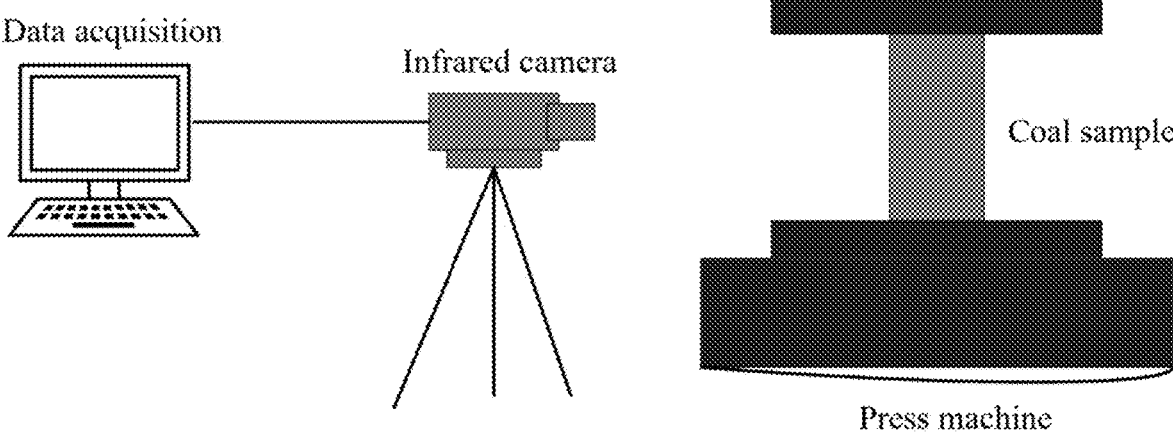
FIG. 9
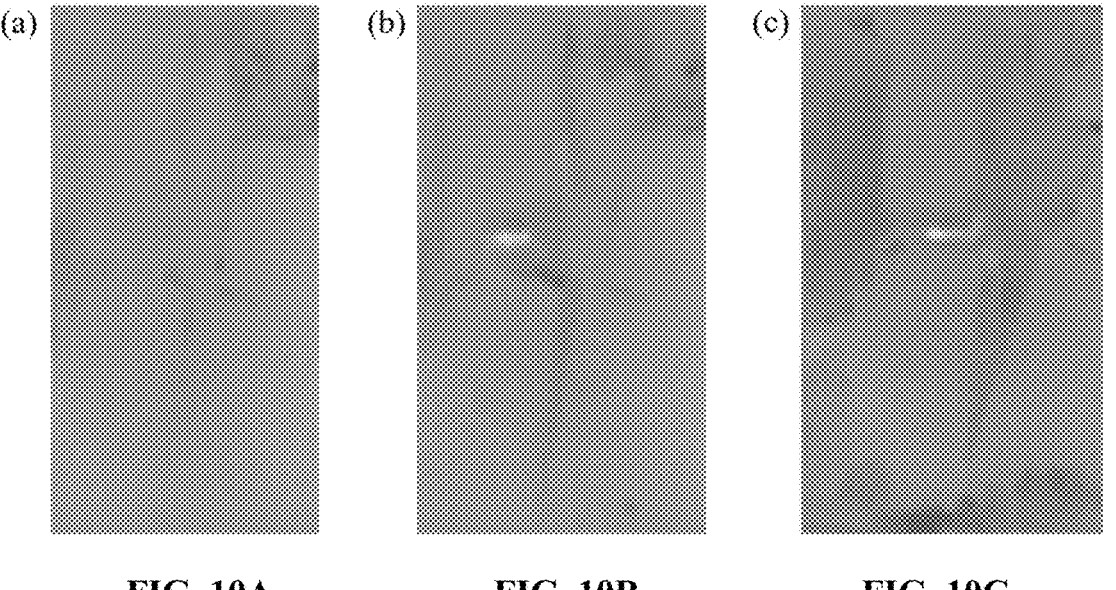
FIG. 10A          FIG. 10B          FIG. 10C

(a) Original image (b) Rotate (c) Translate (d) Scale (e) Crop

DETECTION METHOD FOR INFRARED THERMAL IMAGE DAMAGE AREA OF COAL ROCK

CROSS REFERENCE TO THE RELATED APPLICATIONS

This application is based upon and claims priority to Chinese Patent Application No. 202311037199.0, filed on Aug. 17, 2023, the entire contents of which are incorporated herein by reference.

TECHNICAL FIELD

The invention belongs to the field of damage and fracture detection technology of coal rock, especially relates to a detection method for an infrared thermal image damage area of a coal rock.

BACKGROUND

Coal-rock dynamic disasters are induced by the damage evolution of non-uniform and discontinuous complex geological media under various coupling effects. Coal-rock damage and destruction activities are the precursors before the occurrence of coal-rock dynamic disasters, which are essentially caused by the disturbance of stress field during coal mining. In order to realize the timely early warning of coal-rock dynamic disasters, it is necessary to study the law of disaster occurrence, strengthen the monitoring of coal-rock damage and destruction activities, and find feasible early warning methods. In the process of instability and failure of coal rock, the energy contained in coal will be released outward, which will cause changes in physical quantities such as temperature, acoustic emission, infrared radiation, etc., resulting in a variety of methods such as infrared thermal imaging method and acoustic emission method to observe coal-rock deformation and failure activities. As a widely used non-destructive technology, the infrared thermal imaging method has many advantages such as high reliability, good accuracy, low cost and strong real-time performance in the detection of coal-rock dynamic disasters, it can capture the coal rock and the infrared characteristics destroyed by the coal rock. Specifically, infrared thermal imaging calculates the temperature value of each position by receiving the infrared radiation emitted by the target to be detected, and presents the temperature distribution according to the images of different colors corresponding to different temperatures, so as to find the abnormal temperature area, realize the detection of the damage area of coal rock, and provide a convenient and quick method for preventing the dynamic disaster of coal rock.

In order to find the quantitative relationship between coal-rock damage and infrared radiation, Ma et al. proposed a quantitative method to experimentally observe various parameters of coal rock during loading. On this basis, a stress and infrared radiation model is established by using infrared counting as a quantitative index, and a quantitative characterization method of coal-rock damage evolution is proposed.

In order to predict the destruction of coal-bearing strata in advance and reduce the loss caused by geological disasters, Khan N M et al., under different loading rates, used the two parameters of variance infrared temperature and variance infrared image temperature as indicators, applied the critical slowing theory to carry out the early destruction precursor prediction experiment of coal rock. Gao et al. conducted in-depth research on the coal-rock fracture precursor, and adopted a new infrared analysis method called exponential infrared image entropy, and discussed the variation law of exponential infrared image entropy in combination with infrared image frequency histogram. The experimental results show that the exponential infrared image entropy can effectively characterize the infrared radiation information of coal rock in the process of loading before reaching the peak, and it is found that the abnormal infrared radiation changing from single peak to double peak may be the key precursor before coal-rock destruction. Aiming at the coal-rock dynamic disasters caused by composite mining, combined with the theory of multiple disciplines, Li et al. established the thermodynamic coupling model of composite coal rock under unloading conditions and the simulation model that can carry out numerical simulation. The variation law of infrared radiation of composite coal rock under triaxial loading and unloading conditions is analyzed and verified by experiments. The results show that the infrared radiation temperature is different under different stress conditions, which can provide a theoretical basis for the prevention and control of dynamic disasters in coal-rock mining.

At present, it has become a trend to combine deep learning with infrared thermal imaging for damage detection, but there are relatively few studies on coal-rock damage detection. There are mainly the following problems:

(1) Different from the traditional image segmentation task, the difference between the damage area and the background area in the infrared image segmentation task is small, especially at the edge position, and the temperature change difference is small, which makes it difficult to distinguish. Moreover, the infrared thermal image generated by the infrared thermal imager often contains a lot of noise, which is easy to cover the unobvious damage area, resulting in inevitable missed detection and false detection.

(2) The existing segmentation algorithms have poor generalization, and the segmentation accuracy is very different for different segmentation tasks. The feature extraction ability of the existing algorithms needs to be strengthened, and there is a lack of algorithms for coal-rock damage area segmentation. Therefore, it is necessary to improve the existing algorithms to solve the problem of weak robustness of the algorithms.

SUMMARY

The purpose of the invention is to provide a detection method for an infrared thermal image damage area of a coal rock. The dense residual image denoising algorithm of autocorrelation network and the coal-rock infrared thermal image damage area segmentation algorithm of the improved encoder-decoder network solve the problems of poor denoising effect and low segmentation accuracy of existing technologies.

In order to achieve the above purpose, the invention provides the detection method for the infrared thermal image damage area of the coal rock, including the following steps:

Step 1: collecting and recording an infrared thermal image of the coal rock in a process of loading destruction;

Step 2: processing a gray-scale transformation on the collected infrared thermal image of the coal rock;

Step 3: denoising the infrared thermal image of the coal rock after the gray-scale transformation by the dense residual image denoising algorithm of an autocorrelation network;

Step 4: conducting an area segmentation on the infrared
thermal image of the coal rock after denoising to
extract eigenvalues by using a coal-rock infrared ther-
mal image damage area segmentation algorithm of an
improved encoder-decoder network;

Step 5: observing a damage area of the coal rock.

Preferably, the dense residual image denoising algorithm
of the autocorrelation network in step 3 includes an asym-
metric multi-scale convolution module, a dense residual
cascaded autocorrelation block and a reconstruction module,
and a global residual connection and a skip connection are
also introduced.

Preferably, a specific process of the dense residual image
denoising algorithm of the autocorrelation network in step 3
includes:

S3-1, extracting shallow features from a coal-rock infra-
red thermal image with noise through the asymmetric
multi-scale convolution module, and extracting accu-
rate detailed features in the infrared thermal image of
the coal rock.

S3-2, using the dense residual cascaded autocorrelation
block to further extract deep features;

S3-3, splicing the shallow features extracted by the asym-
metric multi-scale convolution module with the deep
features extracted by the dense residual cascaded auto-
correlation block by using the skip connection; and S3-4, using the reconstruction module to reconstruct a
network to obtain a denoised image, during reconstruc-
tion, using a 3×3 convolutional layer to adaptively
adjust fusion features, and introducing the global
residual connection to learn residual information
between images.

Preferably, the dense residual cascaded autocorrelation
block is densely and skippingly connected by several con-
tinuous autocorrelation blocks, and the autocorrelation block
simulates a three-dimensional convolution with a two-di-
mensional structure.

Preferably, a calculation process of the autocorrelation
block is as follows:

① For a feature map X with a dimension of H×W×C,
one-dimensional fast convolution is used to extract a
correlation of elements, one-dimensional fast convolu-
tion uses one-way local connected convolution, which
only considers an interaction between each node and
adjacent k nodes of each node, and calculates each
feature vector separately.

$$\omega_i = \sigma\left(\sum_{j=1}^{k} w^j e_i^j\right) \tag{1}$$

In a formula, $e_i$ is a node in a feature, the number of nodes
is a size of the feature map, w is a weight for learning, σ is
a Sigmoid function, and $\omega_i$ is an output autocorrelation
weight;

② A correlation of all elements in horizontal, vertical and
channel directions is extracted for each position, and
lengths are w, h and c respectively.

$$\left[y_i^{\hat{H}}, y_j^{\hat{W}}, y_k^{\hat{C}}\right] = F\left(\left[y_i^{\hat{h}}, y_j^{\hat{w}}, y_k^{\hat{c}}\right]\right), y_{i,j,k}, \in X \tag{2}$$

In a formula, $$\left[y_i^{\hat{h}}, y_j^{\hat{w}}, y_k^{\hat{c}}\right]$$

represents an original feature vector in three directions, and
F is a one-dimensional fast convolution function, $$\left[y_i^{\hat{H}}, y_j^{\hat{W}}, y_k^{\hat{C}}\right]$$

is the correlation captured without changing the length, and
the feature vectors in different directions share convolution
parameters independently.

③ One-dimensional convolution traverses the entire fea-
ture map X.

$$Y^{\hat{H}} = \left\{y_0^{\hat{H}}, y_1^{\hat{H}}, y_2^{\hat{H}}, \dots, y_{c \times h}^{\hat{H}}\right\} \tag{3}$$

$$Y^{\hat{W}} = \left\{y_0^{\hat{W}}, y_1^{\hat{W}}, y_2^{\hat{W}}, \dots, y_{c \times w}^{\hat{W}}\right\} \tag{4}$$

$$Y^{\hat{C}} = \left\{y_0^{\hat{C}}, y_1^{\hat{C}}, y_2^{\hat{C}}, \dots, y_{w \times h}^{\hat{C}}\right\} \tag{5}$$

In the formula, $Y^{\hat{H}}$, $Y^{W}$, $Y^{C}$ represent all the feature
vectors in three directions respectively;

④ Conducting a feature splicing in a channel, and
conducting an adaptive feature fusion.

Preferably, a specific process of the coal-rock infrared
thermal image damage area segmentation algorithm of
improved encoder-decoder network in step 4 includes:

S4-1, in an encoder, inputting an image with a size of
256×256 and a number of channels of 1, after feature
extraction by two 3×3 convolutions, using a 2×2 maxi-
mum pooling to downsample and compress the fea-
tures, after four repetitions, inputting a feature map
with rich semantic information at this time into a series
empty space pyramid pooling module to further extract
multi-scale semantic information of the feature map.

S4-2, in a decoder, inputting the feature map output by the
series empty space pyramid pooling module after sam-
pling and the feature map with a corresponding scale
size of the decoder into an attention feature fusion
module to replace an original skip connection; and S4-3, obtaining a feature map with an original size, and
transforming a predicted structure obtained by a feature
vector mapping into a probability distribution map
through 1×1 convolution, wherein the probability dis-
tribution map is input into a dense conditional random
field to further optimize segmentation results.

Preferably, the series empty space pyramid pooling mod-
ule connects dilated convolutions of different expansion
coefficients in series to fill a gap of dilated convolution.

Therefore, the invention adopts the above detection
method for infrared thermal image damage area of coal rock,
which has the following beneficial effects:

(1) Dense residual image denoising algorithm based on
autocorrelation network is used to remove noise in the
infrared thermal image, the algorithm uses asymmetric
multi-scale convolution module to extract features for
the first time, and divides convolution into asymmetric
structure to reduce the number of model parameters.
The algorithm uses autocorrelation block to further
extract features, uses one-dimensional fast convolution
to unify channel and spatial autocorrelation, and it
simulates three-dimensional convolution in a two-di-
mensional structure to achieve lightweight while mak-
ing features contain richer information. In order to
strengthen the propagation of features, the autocorre-
lation blocks are conducted by dense residual connection, and the features of each layer are fully mined to obtain better denoising result.

(2) The coal-rock infrared thermal image damage area segmentation algorithm based on the improved encoder-decoder network. Because the U-Net network has a good performance in the small sample image segmentation task, the U-Net network is selected as the base network and improved to accurately segment the damage area from the coal-rock infrared thermal image. In this paper, the convolution module between the encoder and the decoder is replaced by a series empty space pyramid pooling module, which expands the network receptive field without adding additional parameters and enhances the ability to obtain feature information. The attention feature fusion module is introduced in the skip connection to strengthen the fusion of deep and shallow semantic information, while effectively using the features, the features are screened to strengthen the extraction of the features of the damaged area and improve the accuracy of the segmentation. The dense conditional random field is used for post-processing optimization to optimize the segmentation result and solve the problem of edge blur.

The following is a further detailed description of the technical scheme of the invention through drawings and embodiments.

BRIEF DESCRIPTION OF THE DRAWINGS

FIG. 9 is the experimental system diagram of the invention;

FIGS. 10A-10C are the infrared thermal images of the coal sample in different destruction periods, where FIG. 10A is the infrared thermal image at the initial stage of loading, FIG. 10B is the infrared thermal image at the middle stage of loading, and FIG. 10C is the infrared thermal image at the later stage of loading.

FIG. 11A is the original image, FIG. 11B is the rotation image, FIG. 11C is the translation image, FIG. 11D is the zoom image, and FIG. 11E is the clipping image;

DETAILED DESCRIPTION OF THE EMBODIMENTS

Embodiment

Figure 1:
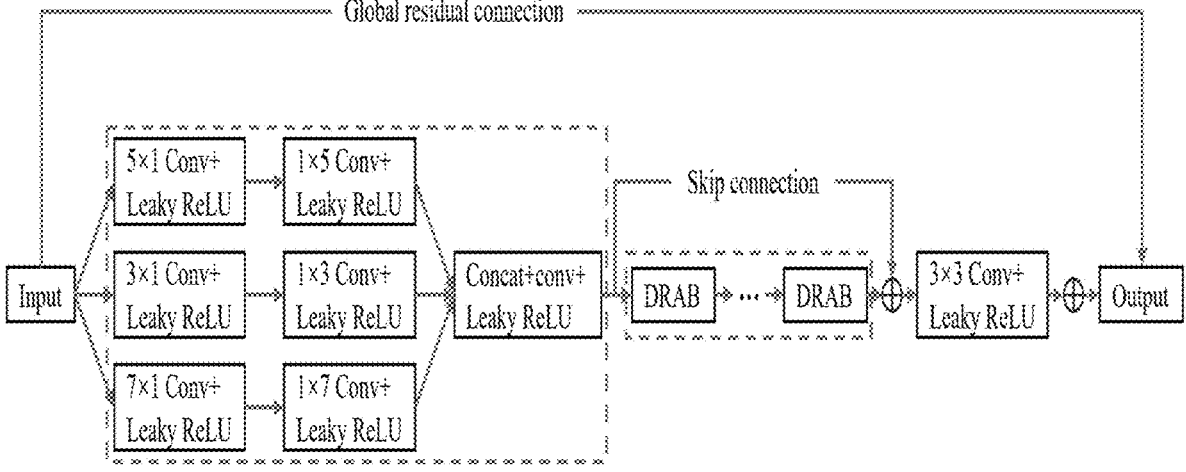
FIG. 1 is the structure diagram of the autocorrelation network model of the invention.
Figure 2:
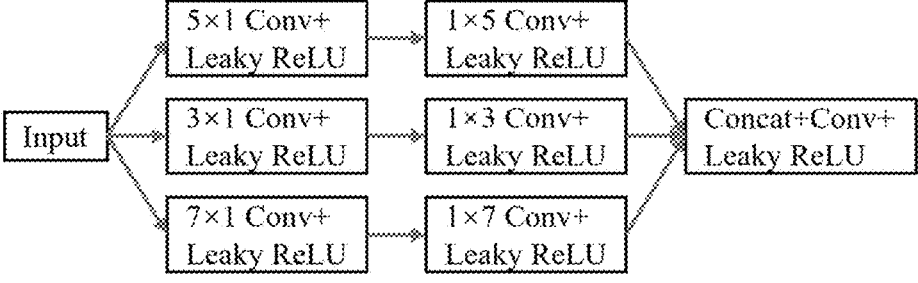
FIG. 2 shows the asymmetric multi-scale convolution module of the invention.
Figure 3:
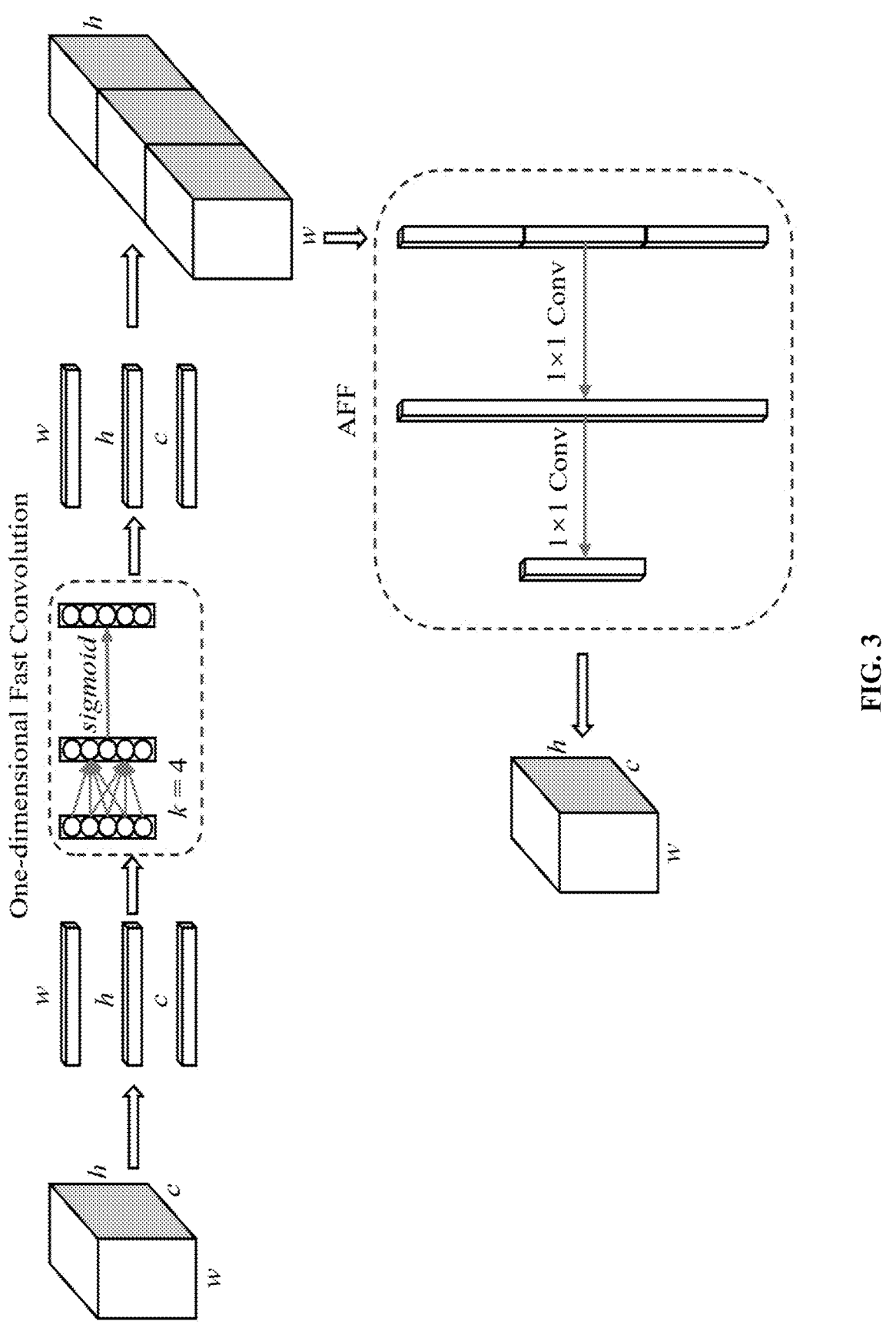
FIG. 3 is the autocorrelation block structure diagram of the invention.
Figure 4:
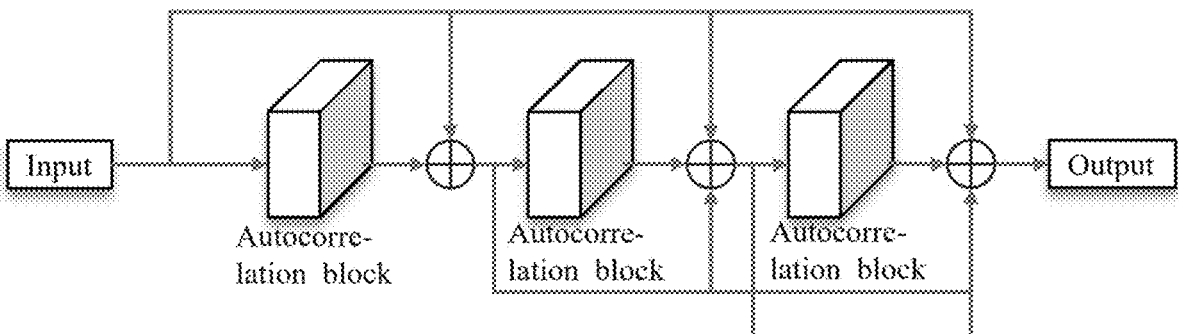
FIG. 4 is the structure diagram of the dense residual autocorrelation block of the invention.
Figure 5:
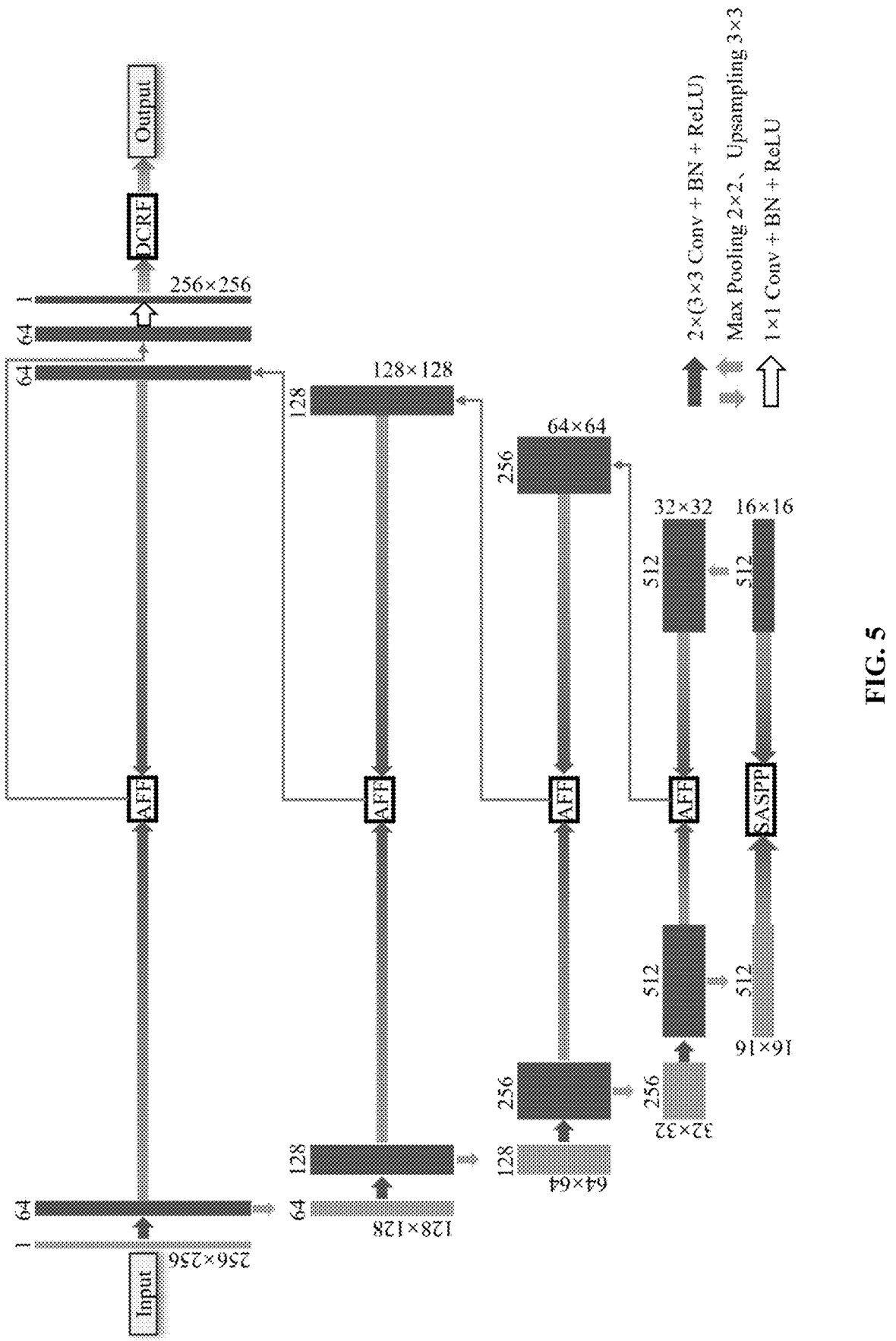
FIG. 5 is the improved U-Net network structure diagram of the invention.
Figure 6:
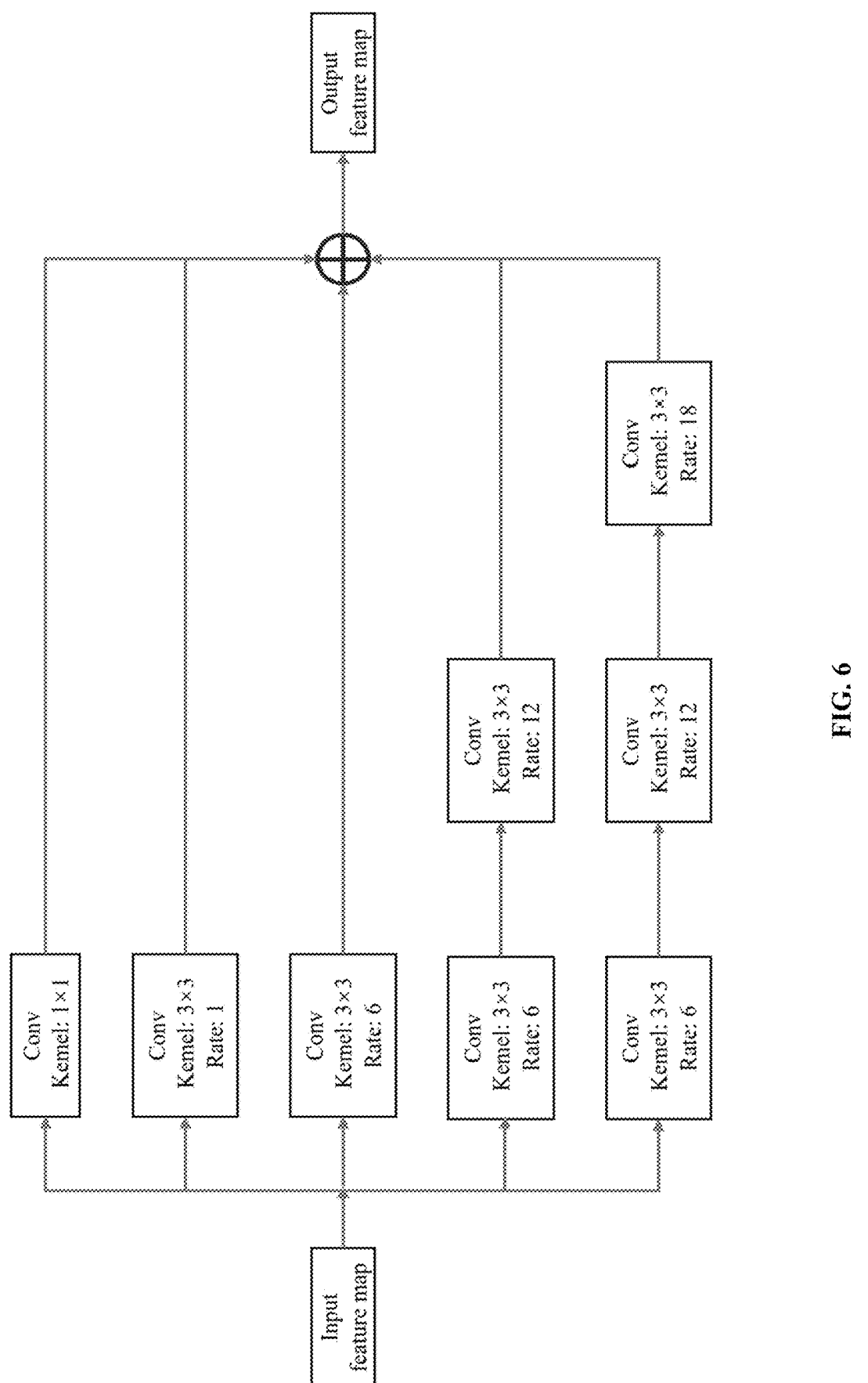
FIG. 6 shows the series empty space pyramid pooling module of the invention.
Figure 7:
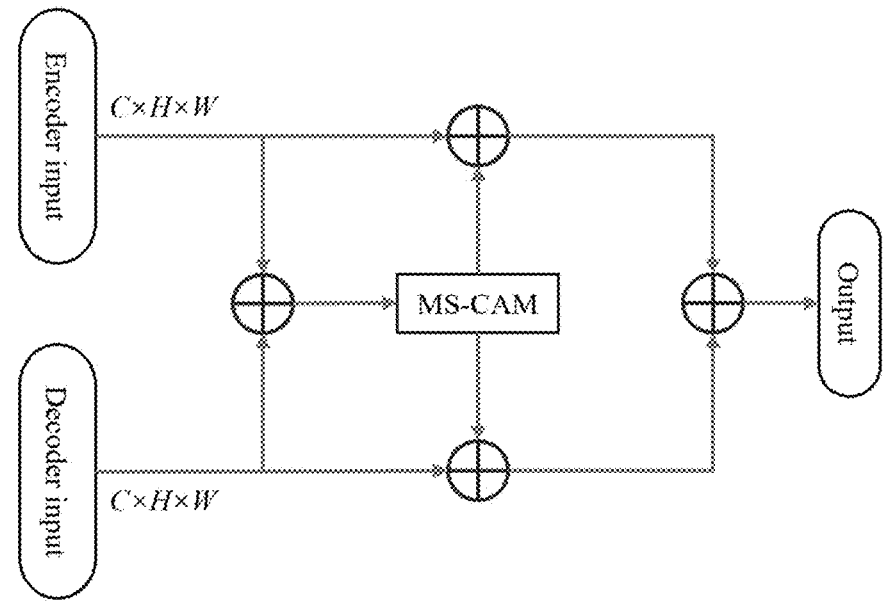
FIG. 7 shows the attention feature fusion module of the invention.
Figure 8:
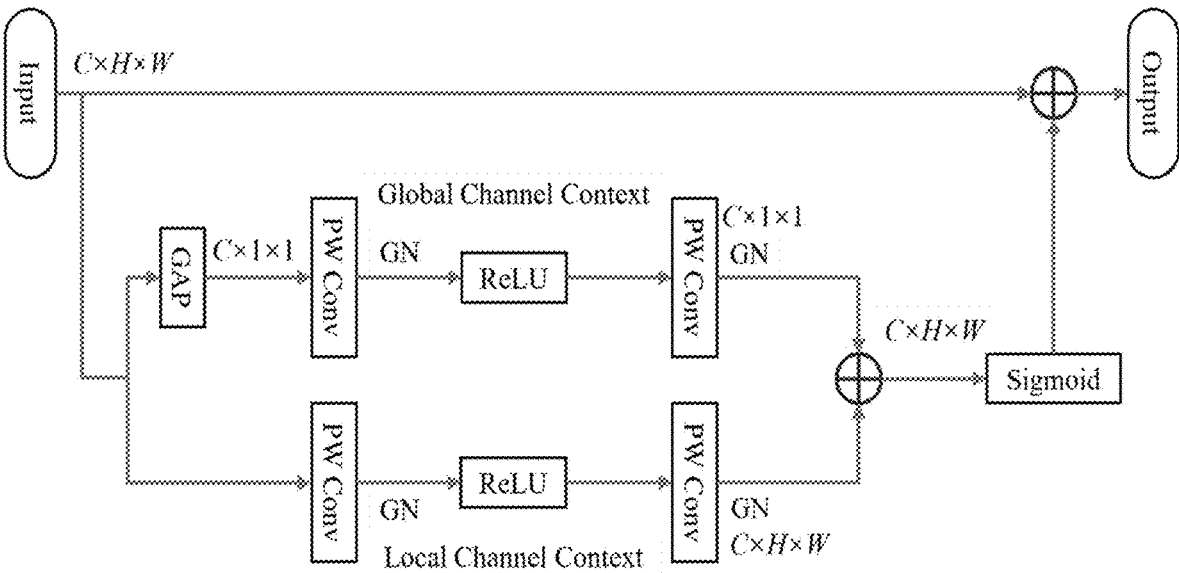
FIG. 8 shows the MS-CAM module of the invention.
Figures 11A, 11B, 11C, 11D, 11E:
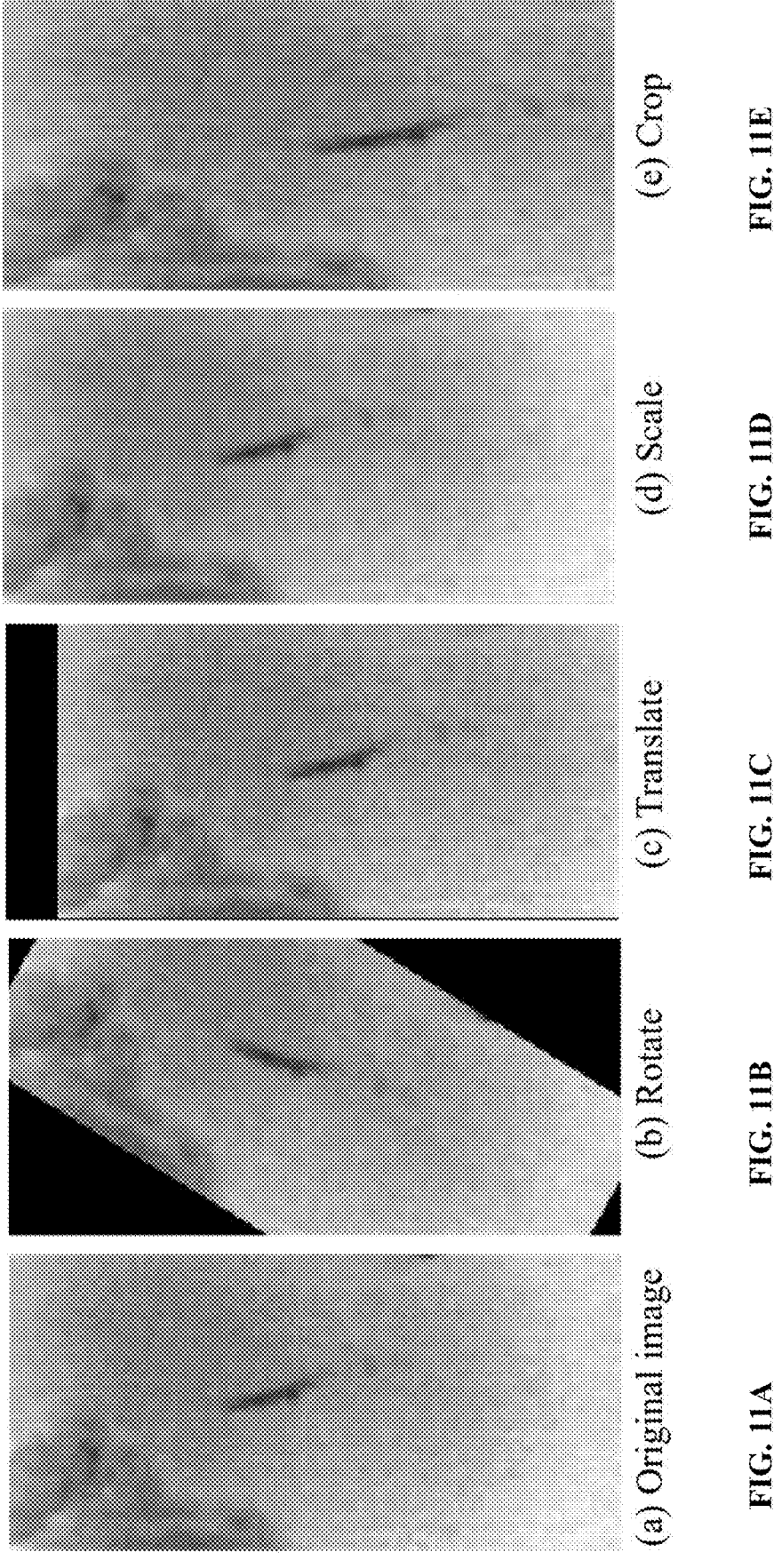
FIGS. 11A-11E are the enhanced images of the data of the invention, where

The following detailed description of the embodiment of the invention provided in the accompanying diagram is not intended to limit the scope of the invention requiring protection, but merely indicates the selected embodiment of the invention. Based on the embodiment of the invention, all other embodiments obtained by ordinary technicians in this field without making creative labor belong to the protection scope of this invention.

Refer to FIGS. 1-8, a detection method for an infrared thermal image damage area of a coal rock, including the following steps:

Step 1: collecting and recording the infrared thermal image of coal rock in the process of loading destruction;

Step 2: processing a gray-scale transformation on the collected infrared thermal image of coal rock;

Step 3: denoising the infrared thermal image of coal rock after the gray-scale transformation by the dense residual image denoising algorithm of autocorrelation network.

Step 4: conducting an area segmentation on the infrared thermal image of coal rock after denoising to extract eigenvalues by using a coal-rock infrared thermal image damage area segmentation algorithm of improved encoder-decoder network.

Step 5: observing the damage area of coal rock.

The specific process of the dense residual image denoising algorithm of autocorrelation network in step 3 is as follows:

S3-1, extracting shallow features from the coal-rock infrared thermal image with noise through the asymmetric multi-scale convolution module, and extracting accurate detailed features in the infrared thermal image of coal rock.

S3-2, using the dense residual cascaded autocorrelation block to further extract deep features, the dense residual cascaded autocorrelation block is densely and skippingly connected by several continuous autocorrelation blocks, and the autocorrelation blocks are simulated by two-dimensional structure to simulate three-dimensional convolution.

S3-3, splicing the shallow features extracted by the asymmetric multi-scale convolution module with the deep features extracted by the dense residual cascaded autocorrelation block by using the skip connection;

S3-4, using the reconstruction module to reconstruct a network to obtain a denoised image, during reconstruction, using a 3×3 convolutional layer to adaptively adjust fusion features, and introducing the global residual connection to learn residual information between images.

The calculation process of the autocorrelation block is as follows:

① For a feature map X with a dimension of H×W×C, a one-dimensional fast convolution is used to extract a correlation of elements, the one-dimensional fast convolution uses one-way local connected convolution, which only considers an interaction between each node and its adjacent k nodes, and calculates each feature vector separately.

$$\omega_i = \sigma\left(\sum\nolimits_{j=1}^{k} w^j e_i^j\right) \tag{1}$$

In a formula, $e_i$ is a node in the feature, the number of nodes is the size of the feature map, w is a weight for learning, $\sigma$ is a Sigmoid function, and $\omega_i$ is an output autocorrelation weight;

② The correlation of all elements in horizontal, vertical and channel directions is extracted for each position, and the lengths are w, h and c respectively.

$$\left[ y_i^{\hat{H}}, y_j^{\hat{W}}, y_k^{\hat{C}} \right] = F\left( \left[ y_i^{\hat{h}}, y_j^{\hat{w}}, y_k^{\hat{c}} \right] \right), y_{i,j,k}, \in X \qquad (2)$$

In the formula, $$\left[ y_i^{\hat{h}}, y_j^{\hat{w}}, y_k^{\hat{c}} \right]$$

represents an original feature vector in three directions, and F is the one-dimensional fast convolution function, $$\left[ y_i^{\hat{H}}, y_j^{\hat{W}}, y_k^{\hat{C}} \right]$$

is the correlation captured without changing the length, and the feature vectors in different directions share convolution parameters independently.

③ One-dimensional convolution traverses the entire feature map X.

$$Y^{\hat{H}} = \left\{ y_0^{\hat{H}}, y_1^{\hat{H}}, y_2^{\hat{H}}, \dots, y_{c \times h}^{\hat{H}} \right\} \qquad (3)$$

$$Y^{\hat{W}} = \left\{ y_0^{\hat{W}}, y_1^{\hat{W}}, y_2^{\hat{W}}, \dots, y_{c \times w}^{\hat{W}} \right\} \qquad (4)$$

$$Y^{\hat{C}} = \left\{ y_0^{\hat{C}}, y_1^{\hat{C}}, y_2^{\hat{C}}, \dots, y_{w \times h}^{\hat{C}} \right\} \qquad (5)$$

In the formula, $Y^{\hat{H}}$, $Y^{\hat{W}}$, $Y^{\hat{C}}$ represent all the feature vectors in three directions respectively;

④ conducting a feature splicing in the channel, and conducting an adaptive feature fusion.

The specific process of the coal-rock infrared thermal image damage area segmentation algorithm of improved encoder-decoder network in step 4 is as follows:

S4-1, in the encoder, inputting an image with a size of 256×256 and a number of channels of 1, after feature extraction by two 3×3 convolutions, using a 2×2 maximum pooling to downsample and compress the features, after four repetitions, inputting the feature map with rich semantic information at this time into a series empty space pyramid pooling module to further extract multi-scale semantic information of the feature map, the series empty space pyramid pooling module connects the dilated convolutions with different expansion coefficients in series to fill the gap of the dilated convolution.

S4-2, in the decoder, inputting the feature map output by the series empty space pyramid pooling module after sampling and the feature map with a corresponding scale size of the decoder into an attention feature fusion module to replace an original skip connection;

S4-3, obtaining a feature map with an original size, and transforming a predicted structure obtained by a feature vector mapping into a probability distribution map through 1×1 convolution, which is input into a dense conditional random field to further optimize segmentation results.

In order to verify the accuracy of the method, the following test is carried out:

In the process of identifying the damage area of coal rock, the German Optris PI450 infrared thermal imager is selected, which has an optical resolution of 382×288 and a measurement speed of 80 Hz, so that it can provide high-speed real-time infrared thermal image. The pressure machine is a YAW4306 microcomputer controlled electro-hydraulic servo pressure testing machine, and the data collector is a computer, which collects and records the infrared thermal image during the load destruction process, the experimental system is shown in FIG. 9.

In the experiment, the coal sample is processed into a rectangular coal sample with a growth×width×height of 50 mm×50 mm×100 mm, and the load destruction is carried out under uniaxial compression, the experimental results are recorded by an infrared thermal imager, the frame is saved as an infrared thermal image and the data set is produced. In order to improve the model's ability to identify different damage areas, some coal samples are subjected to load destruction after prefabricated crack.

The experimental results recorded by the infrared thermal imager are saved, the infrared thermal images of the coal sample when macroscopic damage occurs at the initial stage of loading, coal sample when crack expands at the middle stage of loading and coal sample when the damage is aggravated at the later stage of loading. A total of 300 images are collected. FIGS. 10A-10C show the infrared thermal images of coal samples in three different loading periods.

After completing the data acquisition, the first step is to perform gray-scale transformation on the collected infrared thermal image to reduce the image space and improve the processing speed of the computer. And because the data collected in this paper is relatively small, it is easy to cause the problem of overfitting in the process of model training, in order to solve the problem of overfitting and improve the robustness of the model, the data augmentation method is used to expand the data set. The data enhancement methods used in this paper include rotation, translation, scaling, clipping and other operations, these operations will not change the characteristics of the original data, the image after data enhancement is shown in FIGS. 11A-11E.

After data enhancement, the data set is expanded to 2000, because the data set needs to be labeled when training the segmentation model. In this paper, the label tool LabelMe is used to label the damage area of the collected infrared thermal image of coal rock. Firstly, the infrared thermal image of coal rock is combined with the actual coal sample under the current loading condition to determine the damage area. Then, the image to be labeled is opened in LabelMe, and the segmentation points are created around the damaged area, multiple segmentation points form a polygonal closed-loop area, thereby completing the pixel-level labeling of the image. Finally, the reservation label is marked. The labeled results will be saved as a Json file, which saves the labeled data and converts the Json file into a png file that can be processed by the segmentation model.

The specific content of the environment configuration is shown in Table 1.

TABLE 1

Experimental environment.

| Name | Environmental parameter |
|---|---|
| Experimental operating system | Windows 10 64-bit |
| Experimental Development Tool | PyCharm |
| Processor | AMD R7 7800H |

9

Experimental environment.

| Name | Environmental parameter |
|------|------------------------|
| GPU | NVIDIA Geforce GTX 3060 |
| Deep learning framework | Pytorch |
| Script language | Python |
| Run memory | 16G |

The loss function determines the goal of model training, the training data of the denoising model is an image with noise, and the residual mapping is obtained by residual learning, finally, the denoised image is output, the loss function used in this paper is as shown in (13):

$$L(\theta) = \frac{1}{2N}\sum_{i=1}^{N} \|R(y_i) - (y_i - x_i)\|^2 \quad (13)$$

wherein $y_i$ represents the image with noise, $x_i$ represents the denoised image, $(y_i-x_i)$ represents the noise, $\theta$ is the set of optimization parameters, $R(y_i)$ represents the estimated noise residual, and $L(\theta)$ represents the mean square error between the estimated noise residual and the real noise.

In order to get the minimum value of $L(\theta)$, this paper uses Adam optimization algorithm to update the parameters, the initial learning rate of the model is 0.001, the training batch size is 32, the weight coefficient is regularized and set to 0.001, and the number of training rounds is 200.

In the segmentation model, the cross entropy loss function in the original U-Net network is replaced, and the Focal Loss function is used to solve the problem of unbalanced number of positive and negative samples, so as to realize the reasonable distribution of weight, the expression is as shown in formula (14):

$$L = -\alpha y(1 - p_i)^\gamma \log(p_i) - (1 - \alpha)(1 - y)p_i^\gamma \log(1 - p_i) \quad (14)$$

Wherein y is the actual label, y=1 is the positive sample, y=0 is the negative sample, and $p_i$ is the predicted value, which ranges from 0 to 1. Focal Loss function adds a weight factor $\gamma$ and a balance factor $\alpha$ on the basis of the original cross entropy loss function. The weight factor $\gamma$ ($\gamma>0$) is used to reduce the calculation of negative sample, so that the network model pays more attention to positive sample. The balance factor $\alpha$ is used to adjust the weight of positive and negative samples. These two parameters need to be adjusted according to the actual task. After the experiment, it is determined that when $\gamma=2$ and $\alpha=0.3$, the experimental effect is better, which can effectively improve the training of the network model.

The experiment uses the Adam optimization algorithm to update the parameters, the initial learning rate of the model is 0.0001, the training batch size is 16, the weight coefficient is regularized and set to 0.001, the number of training rounds is 350, and the MS COCO data set is used for transfer learning.

The method of the invention is compared with other common denoising algorithms such as BM3D, DnCNN, FFDNet and IRCNN, four images in the test set are randomly selected for verification, which are recorded as a, b, c and d respectively, and the objective and subjective evaluation criteria are used. The objective evaluation is quantitatively analyzed by the two indicators of peak signal-to-noise ratio (PSNR) and structural similarity index measurement (SSIM), the experimental results are shown in Table 2 and Table 3. Table 2 shows the PSNR values of four images in the test set after denoising under different levels of Gaussian white noise. Table 3 shows the SSIM values of four images in the test set after denoising under different levels of Gaussian white noise. It can be seen from the two tables that when $\sigma=10$, the average PSNR value of the algorithm in this paper is 37.91 dB, which is 0.53 dB, 0.29 dB, 0.17 dB and 0.15 dB higher than the average PSNR values of BM3D, DnCNN, FFDNet and IRCNN respectively. The average SSIM value is 0.9399, which is 0.0263, 0.0236, 0.0048, 0.0052 higher than other algorithms respectively. When $\sigma=25$, the average PSNR value of the proposed algorithm is 35.84 dB, which is 1.03 dB, 0.31 dB, 0.33 dB and 0.21 dB higher than the average PSNR values of other algorithms respectively. The average SSIM value is 0.9006, which is 0.0574, 0.0051, 0.0007 and 0.0044 higher than other algorithms respectively. When $\sigma=50$, the average PSNR value of the proposed algorithm is 33.71 dB, which is 2.15 dB, 1.13 dB, 0.85 dB and 0.97 dB higher than that of other algorithms respectively. The average SSIM value is 0.8732, which is 0.0207, 0.0149, 0.0028 and 0.0146 higher than that of other algorithms respectively. The average PSNR value and SSIM value of the proposed algorithm under three noise levels are better than other algorithms, especially when the noise level is higher, the effect of the proposed algorithm on the infrared thermal image data set of coal rock is more prominent than other algorithms.

TABLE 2

PSNR values of different algorithms on the test set.

| σ | Method | a | b | c | d | Average |
|---|--------|-----|-----|-----|-----|---------|
| 10 | BM3D | 38.66 | 38.24 | 36.59 | 36.04 | 37.38 |
| | DnCNN | 38.86 | 38.33 | 36.74 | 36.55 | 37.62 |
| | FFDNet | 38.75 | 38.43 | 36.98 | 36.79 | 37.74 |
| | IRCNN | 38.89 | 38.49 | 36.90 | 36.74 | 37.76 |
| | Ours | 39.12 | 38.57 | 37.12 | 36.84 | 37.91 |
| 25 | BM3D | 36.53 | 36.56 | 32.38 | 33.75 | 34.81 |
| | DnCNN | 37.00 | 36.81 | 33.54 | 34.78 | 35.53 |
| | FFDNet | 36.71 | 36.86 | 33.66 | 34.80 | 35.51 |
| | IRCNN | 37.06 | 37.00 | 33.59 | 34.86 | 35.63 |
| | Ours | 37.22 | 37.13 | 33.88 | 35.12 | 35.84 |
| 50 | BM3D | 33.10 | 31.06 | 30.46 | 31.63 | 31.56 |
| | DnCNN | 33.55 | 33.81 | 31.05 | 31.91 | 32.58 |
| | FFDNet | 33.89 | 34.26 | 31.16 | 32.11 | 32.86 |
| | IRCNN | 33.93 | 33.99 | 31.10 | 31.94 | 32.74 |
| | Ours | 35.04 | 35.01 | 31.82 | 32.97 | 33.71 |

TABLE 3

SSIM values of different algorithms on the test set.

| σ | Method | a | b | c | d | Average |
|---|--------|-----|-----|-----|-----|---------|
| 10 | BM3D | 0.9421 | 0.9263 | 0.8942 | 0.8919 | 0.9136 |
| | DnCNN | 0.9455 | 0.9280 | 0.8967 | 0.8948 | 0.9163 |
| | FFDNet | 0.9514 | 0.9527 | 0.9225 | 0.9139 | 0.9351 |
| | IRCNN | 0.9581 | 0.9490 | 0.9172 | 0.9143 | 0.9347 |
| | Ours | 0.9617 | 0.9543 | 0.9272 | 0.9165 | 0.9399 |
| 25 | BM3D | 0.9151 | 0.8925 | 0.7813 | 0.7839 | 0.8432 |
| | DnCNN | 0.9369 | 0.9227 | 0.8434 | 0.8791 | 0.8955 |
| | FFDNet | 0.9408 | 0.9263 | 0.8501 | 0.8823 | 0.8999 |
| | IRCNN | 0.9376 | 0.9236 | 0.8438 | 0.8796 | 0.8962 |
| | Ours | 0.9396 | 0.9287 | 0.8510 | 0.8834 | 0.9006 |
| 50 | BM3D | 0.8892 | 0.8923 | 0.7864 | 0.8422 | 0.8525 |
| | DnCNN | 0.9128 | 0.8995 | 0.7781 | 0.8427 | 0.8583 |
| | FFDNet | 0.9248 | 0.9108 | 0.7946 | 0.8515 | 0.8704 |

TABLE 3-continued

| σ | Method | a | b | c | d | Average |
|---|---|---|---|---|---|---|
| | IRCNN | 0.9096 | 0.8966 | 0.7879 | 0.8401 | 0.8586 |
| | Ours | 0.9245 | 0.9136 | 0.8017 | 0.8529 | 0.8732 |

SSIM values of different algorithms on the test set.

Figure 12:
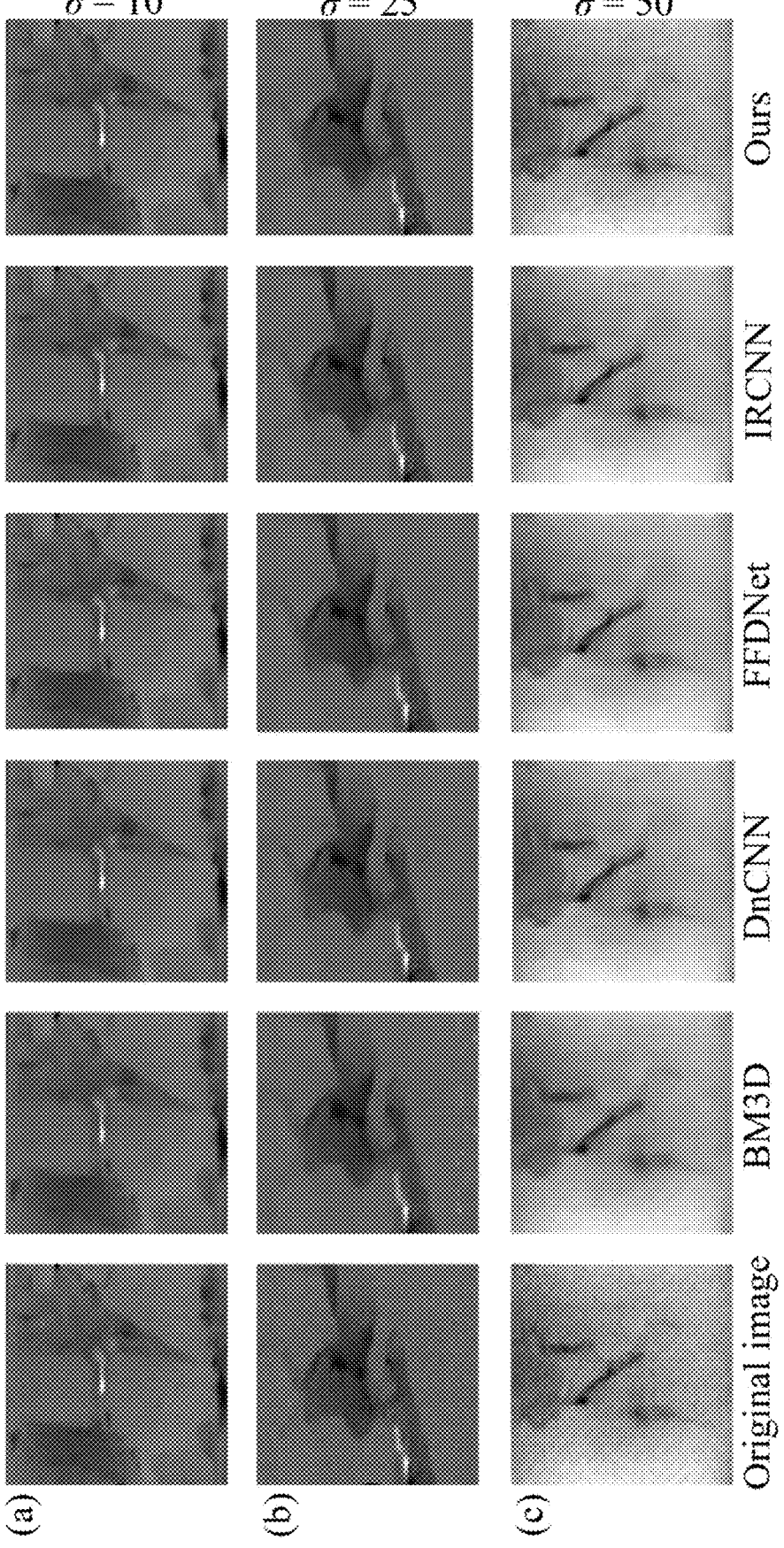
FIG. 12 shows the denoising results of different algorithms under different noise levels.

The experimental results of three images a, b and c under three different levels of Gaussian white noise are selected, as shown in FIG. 12. In FIG. 12, when the first behavior σ=10, a picture is denoised by different algorithms, when the second behavior σ=25, b picture is denoised by different algorithms, when the third behavior σ=50, c picture is denoised by different algorithms. It can be observed that the noise removal of BM3D algorithm is not clean, and there are many defects, there are many noise points in the picture, and the picture looks blurred, so its denoising effect is the worst. The DnCNN algorithm has a better denoising effect than the BM3D algorithm, but there are still some obvious noise residues, and the texture details in the original image are not well preserved. FFDNet and IRCNN have better denoising effect, and there is no obvious noise residue in the picture. However, in the case of high noise level, the texture details in the original image are still lost, and many edge information is erased. Compared with the previous algorithms, the algorithm in this paper preserves the details and structure of the original image well, and the edge information is lost less, which effectively reduces the artifact, so that the image is displayed more clearly and the visual effect is better.

In this paper, a dense residual image denoising algorithm based on autocorrelation network is proposed to preprocess the data set. The experiment shows that the algorithm can effectively remove the noise of infrared thermal image. In order to verify whether the denoising of the infrared thermal image can affect the accuracy of the segmentation, the denoised coal-rock infrared thermal image data set and the original coal-rock infrared thermal image data set are trained on the completed network, and the model is trained to fit under the same parameters. The two experiments are analyzed from the four indicators of accuracy, F1 score, Dice coefficient and MIoU, and the training time is also observed, the experimental results are shown in Table 4.

TABLE 4

Experimental results before and after denoising.

| Network model | Accuracy/ % | F1 score/ % | Dice coeffi- cient/% | MIoU/ % | Training time/ s |
|---|---|---|---|---|---|
| Improved U-Net network (with denoising) | 93.04 | 93.26 | 91.58 | 86.24 | 5372 |
| Improved U-Net network (no denoising) | 92.18 | 92.89 | 90.51 | 84.69 | 6124 |

It can be seen from Table 4 that the neural network model before and after denoising has different segmentation accuracy for coal-rock damage area. Based on the improved U-Net network in this chapter, the accuracy of the model after denoising is 0.86% higher than that of the model without denoising, The F1 score increases by 0.37%, the Dice coefficient increases by 1.07%, the MIoU value increases by 1.55%, and the training time is shortened by 12.28%, it can be seen that the denoising of the infrared thermal image can reduce the noise of the infrared thermal image, reduce the interference of the model, and expand the difference between the damage area and the background to a certain extent. Besides, it can effectively improve the segmentation accuracy of the model for the coal-rock damage area, accelerate the fitting of the model, and significantly reduce the training time of the model.

In order to verify the excellent performance of the improved U-Net network for the segmentation of coal-rock damage area, the algorithm proposed in this paper is compared with U-Net, U-Net++, Atten-UNet, SegNet, FCN-16s, and DeeplabV3+ for coal-rock infrared thermal image data set, and the experimental results are shown in Table 5.

TABLE 5

Experimental results of different algorithms

| Model | Accuracy/ % | F1 score/ % | Dice coefficient/ % | MIoU/ % |
|---|---|---|---|---|
| U-Net | 90.48 | 90.27 | 86.13 | 82.64 |
| U-Net+ + | 90.89 | 91.21 | 86.49 | 84.12 |
| Atten-UNet | 92.53 | 91.97 | 89.26 | 85.44 |
| SegNet | 86.81 | 84.78 | 83.65 | 77.91 |
| FCN-16s | 88.79 | 86.34 | 85.90 | 82.06 |
| DeeplabV3+ | 93.51 | 91.62 | 90.21 | 85.47 |
| Ours | 94.36 | 94.11 | 91.82 | 86.93 |

It can be seen from Table 5 that the algorithm proposed in this paper has achieved excellent results on the coal-rock infrared thermal image data set. The accuracy of the algorithm in this paper has reached 94.36%, the F1 score has reached 94.11%, the Dice coefficient has reached 91.82%, and the MIoU value has reached 86.93%. Compared with the original U-Net network, the accuracy has increased by 3.88%, the F1 score has increased by 3.84%, the Dice coefficient has increased by 5.69%, and the MIoU value has increased by 4.29%. The indicators of the algorithm in this paper are significantly better than the original U-Net network. MIoU is a very important indicator in the image segmentation task. Compared with other algorithms, the MIoU value of the algorithm in this paper is increased by 4.29%, 2.81%, 1.49%, 9.02%, 4.87% and 1.46% respectively. The algorithm in this paper is significantly improved compared with other algorithms, and other indicators have been improved. It shows that the algorithm in this paper can extract and use the target feature information well, balance the damage area and the background area, and can effectively improve the segmentation effect of the coal-rock damage area in the infrared thermal image.

Figure 13:
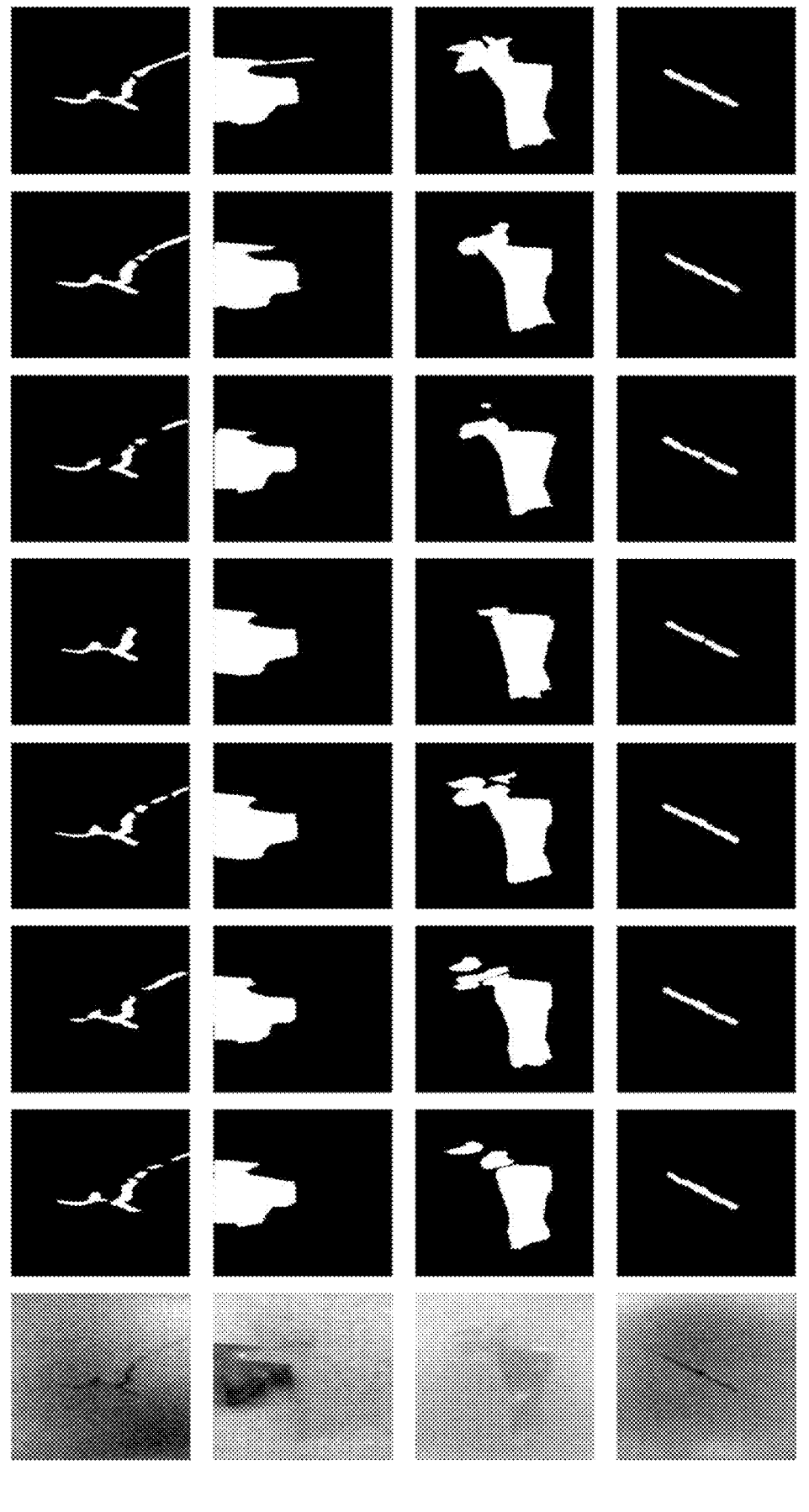
FIG. 13 is the comparison diagram of the segmentation effects of different algorithms of the invention.

FIG. 13 shows the segmentation results of different segmentation algorithms for coal-rock damage area, from the results of detection, the segmentation results of SegNet and FCN-16s are relatively rough, and the phenomenon of missed detection is obvious, SegNet uses VGG to extract features and improves upsampling, but its ability to perceive detailed feature information is poor. FCN-16s uses a convolutional layer with the same scale to extract features, and the receptive field is single, which cannot capture various complex features in the image well, resulting in missed detection. Compared with SegNet and FCN-16s, U-Net has better segmentation result, the receptive field of the feature map obtained by the encoder-decoder structure can cover most of the damaged areas, and the skip connection is introduced, so that the deep and shallow semantic information can be linked together, and the ability to extract detailed feature information can also be improved. U-Net++ and Atten-UNet are improved while retaining the advantages of the original U-Net network, the segmentation results are better than U-Net, a large area of damage area can be well identified and segmented, but for some areas where the damage is not obvious, the recognition effect is poor, and the network structure still has room for improvement. After the Deeplab network is proposed, its structure is continuously improved, the proposed DeplabV3+ uses a spatial pyramid pooling module with dilated convolution can extract multi-scale information in the image and it introduces a decoder module to further fuse the deep and shallow features, which effectively improves the accuracy of segmentation, but there are still a small number of missed detections. Compared with other algorithms, the algorithm proposed in this paper can accurately identify the damage area, and the edge is smoother, it can also achieve accurate segmentation where the damage area and the background are very difficult to distinguish, there is basically no missed detection phenomenon, the segmentation result is consistent with the actual situation, and it can complete the segmentation of the coal-rock damage area well.

Therefore, the invention adopts the above-mentioned detection method for the infrared thermal image damage area of the coal rock, and improves the denoising effect and segmentation accuracy of coal-rock infrared thermal image through the dense residual image denoising algorithm of autocorrelation network and the coal-rock infrared thermal image damage area segmentation algorithm of U-Net network.

Finally, it should be noted that the above embodiments are only used to explain the technical scheme of the invention rather than to restrict it, although the invention is described in detail with reference to the better embodiments, ordinary technicians in this field should understand that they can still modify or replace the technical scheme of the invention, and these modifications or equivalent replacements cannot make the modified technical scheme out of the spirit and scope of the technical scheme of the invention.

The invention claimed is:

1. A detection method for an infrared thermal image damage area of a coal rock, comprising the following steps:
    step 1: collecting and recording an infrared thermal image of the coal rock in a process of loading destruction;
    step 2: processing a gray-scale transformation on the infrared thermal image of the coal rock;
    step 3: denoising the infrared thermal image of the coal rock after the gray-scale transformation by a dense residual image denoising algorithm of an autocorrelation network;
    step 4: conducting an area segmentation on the infrared thermal image of the coal rock after denoising to extract eigenvalues by using a coal-rock infrared thermal image damage area segmentation algorithm of an improved encoder-decoder network; and
    step 5: observing a damage area of the coal rock;
    wherein the dense residual image denoising algorithm of the autocorrelation network in step 3 comprises an asymmetric multi-scale convolution module, a dense residual cascaded autocorrelation block and a reconstruction module, and a global residual connection and a skip connection are also introduced;
    wherein a specific process of the dense residual image denoising algorithm of the autocorrelation network in step 3 comprises:

S3-1, extracting shallow features from a coal-rock infrared thermal image with noise through the asymmetric multi-scale convolution module, and extracting accurate detailed features in the infrared thermal image of the coal rock;
S3-2, using the dense residual cascaded autocorrelation block to further extract deep features;
S3-3, splicing the shallow features extracted by the asymmetric multi-scale convolution module with the deep features extracted by the dense residual cascaded autocorrelation block by using the skip connection; and
S3-4, using the reconstruction module to reconstruct a network to obtain a denoised image, during reconstruction, using a 3×3 convolutional layer to adaptively adjust fusion features, and introducing the global residual connection to learn residual information between images;
wherein a specific process of the coal-rock infrared thermal image damage area segmentation algorithm of the improved encoder-decoder network in step 4 comprises:
S4-1, in an encoder, inputting an image with a size of 256×256 and a number of channels of 1, after feature extraction by two 3×3 convolutions, using a 2×2 maximum pooling to downsample and compress the features, after four repetitions, inputting a feature map with rich semantic information at this time into a series empty space pyramid pooling module to further extract multi-scale semantic information of the feature map;
S4-2, in a decoder, inputting the feature map output by the series empty space pyramid pooling module after sampling and a feature map with a corresponding scale size of the decoder into an attention feature fusion module to replace an original skip connection; and
S4-3, obtaining a feature map with an original size, and transforming a predicted structure obtained by a feature vector mapping into a probability distribution map through 1×1 convolution, wherein the probability distribution map is input into a dense conditional random field to further optimize segmentation results, and the results are output after repeated reasoning.

2. The detection method for the infrared thermal image damage area of the coal rock according to claim 1, wherein the dense residual cascaded autocorrelation block is densely and skippingly connected by several continuous autocorrelation blocks, and the autocorrelation block simulates a three-dimensional convolution with a two-dimensional structure.

3. The detection method for the infrared thermal image damage area of the coal rock according to claim 2, wherein a calculation process of the autocorrelation block is as follows:
    ① for a feature map X with a dimension of H×W×C, a one-dimensional fast convolution is used to extract a correlation of elements, the one-dimensional fast convolution uses one-way local connected convolution, which only considers an interaction between each node and adjacent k nodes of each node, and calculates each feature vector separately:

$$\omega_i = \sigma\left(\sum_{j=1}^{k} w^j e_i^j\right) \tag{1}$$

wherein $e_i$ is a node in a feature, a number of nodes is a size of the feature map, w is a weight for learning, $\sigma$ is a Sigmoid function, and $\omega_i$ is an output autocorrelation weight;

② a correlation of all elements in horizontal, vertical and channel directions is extracted for each position, and lengths are w, h and c respectively:

$$\left[y_i^{\hat{H}}, y_j^{\hat{W}}, y_k^{\hat{C}}\right] = F\left(\left[y_i^{\hat{h}}, y_j^{\hat{w}}, y_k^{\hat{c}}\right]\right), y_{i,j,k}, \in X \qquad (2)$$

wherein $$\left[y_i^{\hat{h}}, y_j^{\hat{w}}, y_k^{\hat{c}}\right]$$

represents an original feature vector in three directions, and F is a one-dimensional fast convolution function, $$\left[y_i^{\hat{H}}, y_j^{\hat{W}}, y_k^{\hat{C}}\right]$$

is the correlation captured without changing the lengths, and feature vectors in different directions share convolution parameters independently;

③ one-dimensional convolution traverses the entire feature map X:

$$Y^{\hat{H}} = \left\{y_0^{\hat{H}}, y_1^{\hat{H}}, y_2^{\hat{H}}, \dots , y_{c \times h}^{\hat{H}}\right\} \qquad (3)$$

$$Y^{\hat{W}} = \left\{y_0^{\hat{W}}, y_1^{\hat{W}}, y_2^{\hat{W}}, \dots , y_{c \times w}^{\hat{W}}\right\} \qquad (4)$$

$$Y^{\hat{C}} = \left\{y_0^{\hat{C}}, y_1^{\hat{C}}, y_2^{\hat{C}}, \dots , y_{w \times h}^{\hat{C}}\right\} \qquad (5)$$

wherein $Y^{\hat{H}}$, $Y^{\hat{W}}$, $Y^{\hat{C}}$ represent all the feature vectors in three directions respectively; and ④ conducting a feature splicing in a channel, and conducting an adaptive feature fusion.

4. The detection method for the infrared thermal image damage area of the coal rock according to claim 3, wherein the series empty space pyramid pooling module connects dilated convolutions of different expansion coefficients in series to fill a gap of dilated convolution.

\* \* \* \* \*